United States Patent [19]

Freire

[11] Patent Number: 5,637,073
[45] Date of Patent: Jun. 10, 1997

[54] RADIATION THERAPY FOR TREATING MACULAR DEGENERATION AND APPLICATOR

[76] Inventor: Jorge E. Freire, 116 Wagonwheel Ct., Marlton, N.J. 08053

[21] Appl. No.: 520,013

[22] Filed: Aug. 28, 1995

[51] Int. Cl.$^6$ ..................................................... A61N 5/00
[52] U.S. Cl. ............................................................... 600/3
[58] Field of Search ...................... 600/1–8; 128/897–98

[56] References Cited

U.S. PATENT DOCUMENTS 5,426,662  6/1995  Mefferd et al. .
5,431,907  7/1995  Abelson et al. .

*Primary Examiner*—John P. Lacyk
*Attorney, Agent, or Firm*—Duane, Morris & Heckscher

[57] ABSTRACT

Radiation therapies and applicators are provided by this invention which are useful in the treatment of macular degeneration in patients. The therapies include providing an applicator sized to fit between a sclera and an eye socket of the patient. A therapeutic quantity of a radioactive substance is disposed in the distal tip of the applicator. This substance has a range of no greater than about 1 cm, or alternatively, is made from $Sr_{90}$. The method includes exposing a portion of the macular tissue of the patient to radiation emitted from the radioactive substance for a time sufficient to fuse a portion of the capillaries located within the neovascular tissue which are responsible for the disease. The therapy is designed to burn off unwanted capillaries and debris without substantially interfering with other important tissues in the patient's eye, such as the lens or optic disc.

20 Claims, 4 Drawing Sheets

RADIATION THERAPY FOR TREATING MACULAR DEGENERATION AND APPLICATOR

FIELD OF THE INVENTION

This invention relates to methods and devices for treating diseases of the retina, and more particularly to radiation therapies and applicators suitable for reducing or limiting the growth of neovascular membranes without substantially damaging other vital tissues which are important to sight.

BACKGROUND OF THE INVENTION

The human eye functions by focusing images of light through a lens and onto a light sensitive, round area of the sensory retina called the macula retinae, often simply called the "macula". A human macula is located temporally from the optic disc and is responsible for receiving optical images from the lens and translating these images into electrical stimuli for delivery through the optic nerve to the brain. The macula can contain up to six million cone cells, tiny biological translators which are helpful in discerning colors, and up to one hundred and twenty million rod cells, which are essential to peripheral vision. When the macula is healthy, it contains a cone-shaped depression called the central fovea which contains many cone cells.

As we get older, the tissue beneath the fovea, called the retinal pigmented epithelium, gradually accumulates molecular debris. This causes changes in the subretinal space and a release of an angiogenic factor that stimulates a neovascular network containing many fine capillaries. This network produces hemorrhagic fluid beneath the fovea, distorts its shape, kills cone cells and results in the eventual loss of central vision and a gradual worsening of visual acuity, commonly called "macular degeneration".

Macular degeneration is a terrifying disease which is the leading cause of legal blindness among older people in the United States and Europe. Macular degeneration is believed to affect about 10% of those between the ages of 65 and 75 and about 30% of those between the ages of 75 and 85. With the life expectancy of the human population increasing every year as a result of better health care, and the aging of the "baby boomer" generation in the United States, it is expected that the first and second decades of the next century will be fraught with a considerable increase in blindness due to this disease.

Modern attempts to alleviate the effects of macular degeneration have included laser and surgical techniques. Although burning the retina membrane with a laser has been effective in temporarily controlling the growth of the neovascular tissue, the capillaries in the tissue tend to resume their growth pattern in about three or four months following laser surgery, requiring more laser doses until the treatments eventually become ineffective. Laser burning techniques are also known to kill more cone cells than the disease does, which is obviously counterproductive.

Surgery, on the other hand, has proven to be successful in dissecting neovascular tissue without substantially affecting the cone cell population. However, even the best surgical technique merely postpones the growth of the disease for about two or three months, after which, more vessels grow into the scarred neovascular tissue and the patient must return for more surgery. Unfortunately, most of these patients also become blind.

In an almost desperate attempt to restore sight to these patients, ionizing radiation is now being used to close off capillaries in the neovascular tissue. Radiation therapy has been tried before, in the treatment of hemangiomas of the choroid, the layer of tissue between the pigmented retina layer and the sclera.

In radiation therapy experiments for treating the macula, a radioactive plaque containing Iodine-125 ("$I_{125}$") has been proposed to be used. $I_{125}$, a common radioactive isotope, is a powerful therapeutic γ-ray, ionized agent which is capable of delivering of a "dose" of about 100 cGr/hr. $I_{125}$ also exhibits a radiation "range" in which about 60% of its dose is delivered at a distance of about one centimeter from the source.

Radiation treatments using $I_{125}$ are slow, requiring two doses of anesthesia over a span of about 10–11 hours. $I_{125}$ also has the unintended effect of irradiating the patient's optic disc and lens, creating the potential for serious side effects, including cataracts.

Accordingly, there is a need for a better therapy for treating macular degeneration. Such a therapy should be safe to use for both health care practitioners and patients. It should also be cost effective and efficacious.

SUMMARY OF THE INVENTION

The present invention provides a method of radiation therapy and an applicator for the treatment of macular degeneration. This disease is known to be caused by the proliferation of neovascular tissue in retinal pigmented epithelium. The applicator of this invention has a distal end portion sized to fit between a patient's sclera and eye lid. Disposed onto this applicator is a therapeutic quantity of a radioactive substance which emits 99% of its radioactivity within a narrow range of less than 1 cm. This therapy also includes exposing a portion of the macular tissue of the patient to the radiation emitted from the radioactive substance for a time sufficient to close off a portion of a plurality of capillaries located within the diseased tissue. This radiation treatment is designed to at least minimize further degeneration of the patient's macula while not substantially irradiating the lens or optic nerve.

The therapies of this invention provide extremely focused radiation treatments which attack the tiny capillaries in the neovascular network beneath the fovea without damaging the optic nerve or clouding the lens of the patient. The preferred radioactive substance of this invention, Strontium-90 ("$Sr_{90}$") is an ideal isotope for treating macular degeneration. It has a half life of twenty-eight years, permitting it to be stored almost indefinitely in a hospital pharmacy. It is a beta emitter having shallow penetration—typically only about 35–40% of its radiation is found at 2 mm. This results in a very focused ionizing beam that spares the remaining retinal tissue around the macula as well as the optic disc and the lens.

The preferred radioactive materials selected by this invention carry a dosage which is at least about 50 cGr/sec, and preferably is within the range of about 60–100 cGy per second. This provides extremely fast treatment. For example, for delivering a dose of 1,000 cGy at a depth of about 1.5–2 milliliters, the entire radiation treatment need not take longer than about two minutes, depending upon the activity of the isotope source.

This invention provides for out-patient and same-day-surgery procedures that minimize the patient's time in the hospital, reduce the possibility of adverse consequences of prolonged anesthesia, and reduce hospital expenses. These inventive therapies will have a prolonged effect in reducing blindness in the elderly population due to macular degeneration and can eliminate the need for repetitive, and decreasingly effective surgeries and laser procedures.

In further embodiments of this invention, a radiation therapy applicator is provided having proximal and distal end portions, in which the distal end portion includes a stem having a cavity. The cavity preferably contains $Sr_{90}$. In addition, this embodiment further includes a selectively removable shield for exposing the $Sr_{90}$ material for delivering a dose of radiation to a diseased tissue portion of a patient's eye.

A BRIEF DESCRIPTION OF THE DRAWINGS

The accompanying drawings will illustrate preferred embodiments of the invention according to the practical application of principles thereof, and in which:

FIG. 1: is a side elevation view of a preferred macular applicator of this invention;

FIG. 2: is a top plan view of the macular applicator of FIG. 1;

FIG. 3: is a partial, cross-sectional view of a distal tip region of the preferred macular applicator of FIG. 1;

FIG. 4: is a diagrammatic, cross-sectional view of the human eye having inserted therein the applicator of this invention for the treatment of macular degeneration;

FIG. 5: is an enlarged view of the macula being treated with the applicator of this invention.

DETAILED DESCRIPTION OF THE INVENTION

Radiation therapies and applicators useful in such therapies are provided by this invention. These therapies and devices are designed to provide a safe and efficient fusing of tiny capillaries in neovascular tissue. Although the applicators of this invention are described as being useful in ophthalmic surgery, it can be readily understood that this invention could have substantial merit in the treatment of various forms of cancer and blockage in portions of the body other than the eye, such as in glands, such as the thyroid; organs, such as the brain; and small lumens, such as coronary arteries. The disclosed radioactive substances and shielding techniques have been specially designed to promote tissue removal in small localized areas without damaging surrounding tissue, making the applicators of this invention highly desirable for use within the human body.

Figure 1:
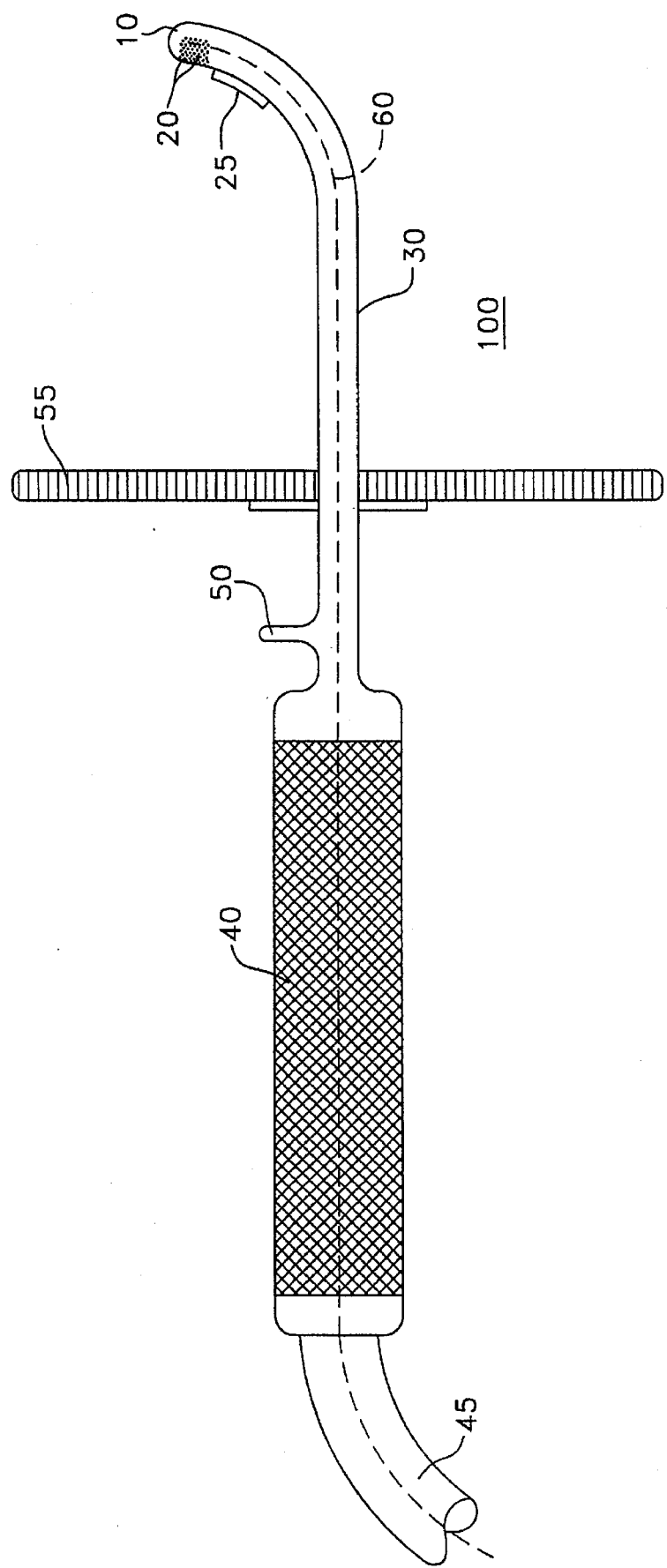
Figure 2:
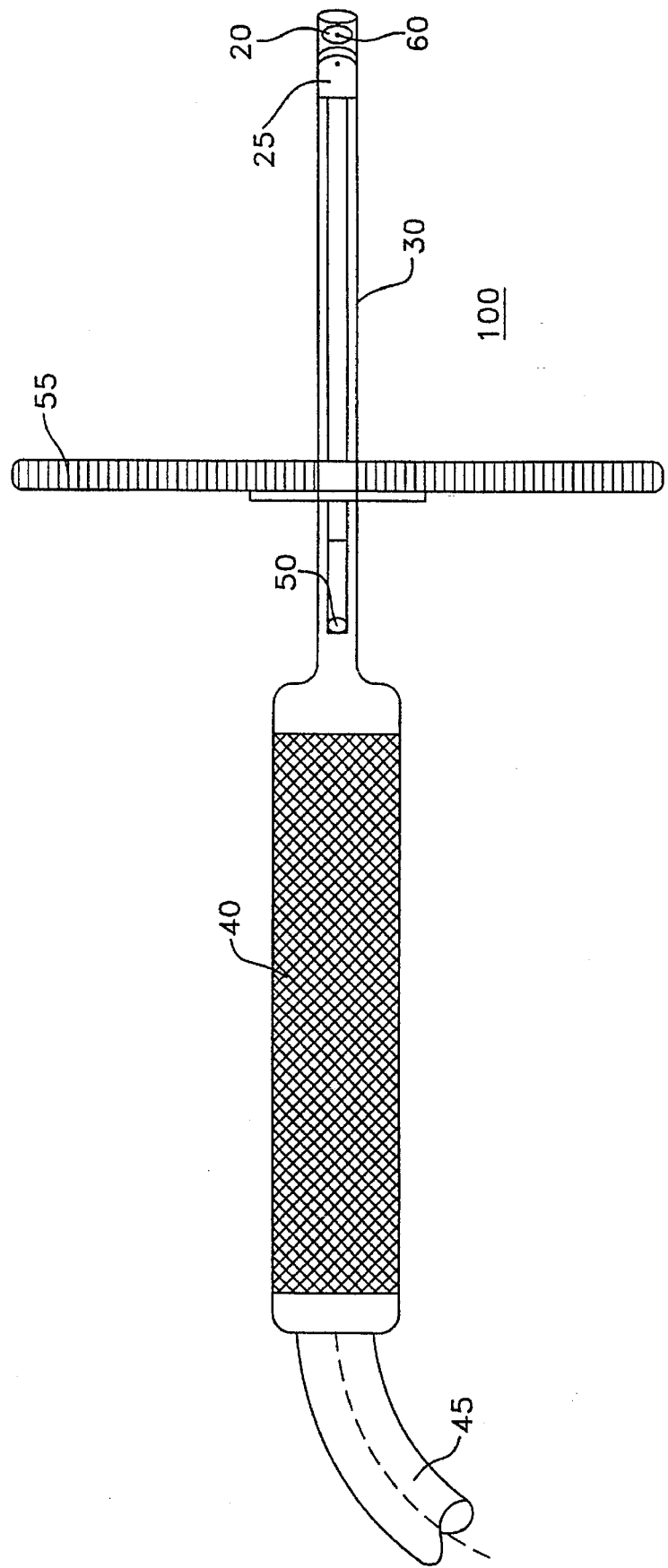
Figure 3:
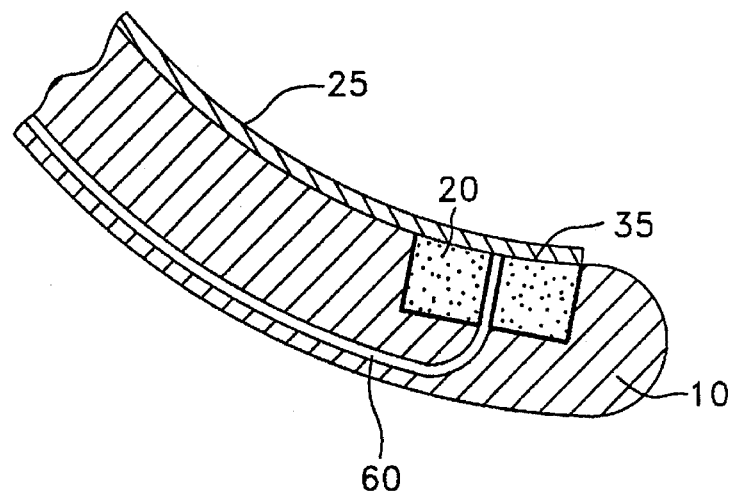

With reference to the figures, and particularly to FIG. 1—3 thereof, there is shown a preferred macular applicator 100 having proximal and distal ends. A handle 40 is located at the proximal end and a cable sleeve 45 extends from the handle 40 for housing a preferred fiber optic cable 60 and image return assembly. At the distal end of the device is located a radioactive compound 20 fitted within a small cavity. The fiber optic cable 60 can be disposed through the radioactive compound 20 so as to provide visible access to diseased tissue while simultaneously locating the compound 20 at the treatment site.

The preferred macular applicator 100 of this invention also includes a sliding shield 25 fitted along the stem 30 of its distal end. The sliding shield 25 contains a shielding material, such as lead (Pb), silver (Ag) or gold (Au), and helps to minimize any inadvertent delivery of radiation doses during storage and while the distal tip 10 of the macular applicator 100 is being inserted between the sclera 190 and eye lid of a patient, as disclosed in FIG. 4. The macular applicator 100 also comprises a hand shield 55, which preferably contains acrylic of 6 mm shielding, so as to protect the health care worker during use.

In the enlarged view of FIG. 3, the relationship between the preferred radioactive compound 20, the fiber optic cable 60 and sliding shield 25 is more clearly portrayed. When the macular region of the retina is located by visually inspecting the posterior surface of the sclera through the fiber optic cable 60, the sliding shield 25 can be manually removed by pushing lever 50 located near the handle 40 of the applicator 100. Once the sliding shield 25 has been pulled back to reveal the radioactive compound 20, fast electrons are discharged for a distance equal to "d", as shown FIG. 5. This measurement should be less than about one centimeter and preferably is less than 5 mm to avoid inadvertently irradiating the optic disc and lens 110. Stated differently, the preferred radioactive compound 20 of this invention is designed to emit 99% of its radioactivity ions within a narrow semi-spherical range of less than 1 cm, and preferably less than 5 mm. The radioactive compound 20 can also include a thin, protective gold layer 35. Typical therapeutic isotopes along with their radioactive properties are disclosed below in Table I.

TABLE 1

| Typical Therapeutic Isotopes | | | | |
|---|---|---|---|---|
| Isotope (Shelf-Life) Half-Life | Isotope | Rays | "Range" | "Dose" Rate/Time | Shielding Comments |
| 5.2 yrs. | $Co_{60}$ | γ | @1 cm ~90% lens gets 40% cataract | ~50 cGr/hr. | Difficult to shield; 1 cm of lead |
| 60 days | $I_{125}$ | γ | @1 cm ~60% | ~100 cGr/hr. | Easy to shield; gold or lead 0.5 mm |
| 70 days | $Ir_{192}$ | γ | @1 cm ~90% | ~60 cGr/hr. | Difficult to shield; 6 mm of lead |
| 360 days | $Rh_{103}$ | β | @1 cm ~10% | 40 cGr/hr. | Easy to shield; silver 1 mm |
| 28.5 yrs. | $Sr_{90}$ | β | @1 cm ~0% | 80–100 cGr/sec. | Easy to shield; .03 mm lead or .3 mm silver |
| 2 weeks | $Pl_{106}$ | γ | @1 cm ~10% | 150–180 cGr/hr. | 1 mm of lead |

This invention prefers to use $Sr_{90}$ because it has a long half life for better storage, low penetration, for not interfering with the optic disc or lens of the patient, and fast acting beta rays which significantly reduce the therapy time for the patient. This invention permits same-hour surgery without extensive anesthesia. Artisans will also note that shielding $Sr_{90}$ is readily provided by about 0.3 mm of silver or 0.03 mm of lead without resorting to thick shielding layers which would enlarge the size of the distal tip of the applicator 100.

Figure 5:
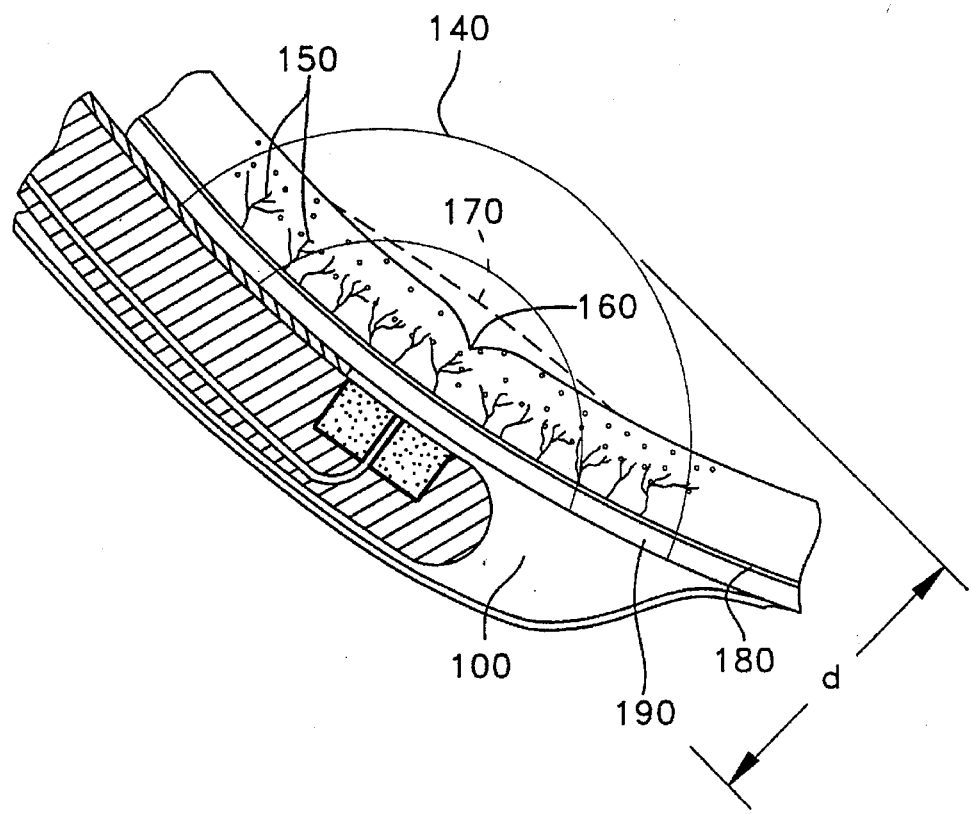
Figure 4:
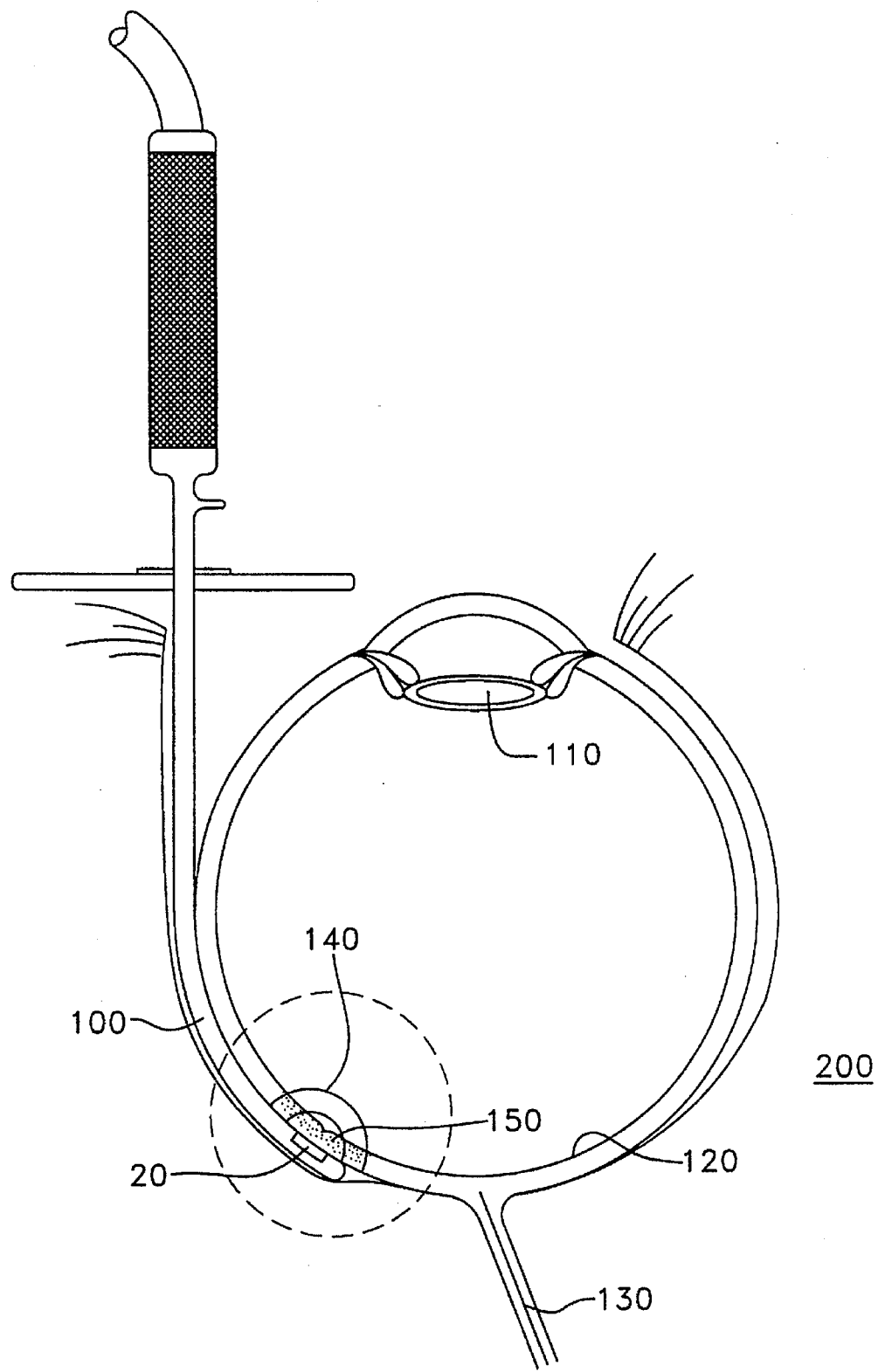

With reference to FIGS. 4 & 5, the preferred method of this invention will now be described. In the preferred therapy embodiment, the delivery of radiation to the macula need not take more that 5 minutes, and preferably is less than two minutes. The patient is briefly anesthetized during the procedure, and the distal tip of the applicator is inserted under the eyelid and behind the eye 200. The pigmented macular region of the retina 120 is located through the fiber optic cable 60 by shining light through the sclera 190 and choroid 180. Upon locating the macula, the sliding shield 95 is slid into the open position so as to expose the neovascular membrane 150 to the effects of the radioactive compound 20. This radiation will burn the small capillaries in the neovascular membrane 150 and substantially close them off to prevent further growth. The fusing of the neovascular capillaries will reverse, or at lease deter, the growth of the distorted retina tissue 170. If sufficient reduction of the neovascular membrane 150 is accomplished, the fovea 160 can be regenerated, or at least retained, and the cone cells of the macular tissue can be preserved for the patient. It is important to note that because of the rather narrow range of β-ray emissions from the preferred radioactive substance, $Sr_{90}$, the lens 110, optic nerve 130 and disc of the patient's eye 200 are not adversely effected. Although no one can predict a complete cure for this disease, it is envisioned that this procedure can substantially control or reduce the propagation of this disease in adults.

From the foregoing, it can be realized that this invention provides improved radiation therapies and applicators for delivering a highly controlled dosage of radiation for removing diseased tissue. The applicators and therapies are highly effective in the treatment for macular degeneration, one of the leading causes of blindness in older people. This invention provides radioactive substances which provide efficient burning of the diseased tissue without inadvertently irradiating surrounding tissue. Because very little scarring is created in the retina of the eye, the further growth of capillaries and neovascular membrane is minimized without the need for further corrective surgery. Although various embodiments have been illustrated, this was for the purpose of describing, but not limiting the invention. Various modifications, which will become apparent to those skilled in the art, are within the scope of this invention described in the attached claims.

What is claimed is:

1. A method of radiation therapy for the treatment of macular degeneration in a patient caused by a proliferation of neovascular tissue comprising:

(a) providing an applicator having a distal end portion sized to fit between a sclera and an eye lid of said patient;

(b) disposing a therapeutic quantity of a radioactive substance onto said applicator, said radioactive substance emitting 99% of its radioactivity within a narrow range of less than 1 cm;

(c) exposing said neovascular tissue of said patient to radiation emitted from said radioactive substance for a time sufficient to close off a portion of a plurality of capillaries located within said neovascular tissue to at least minimize further macular degeneration in said patient while not substantially irradiating said patient's lens or optic nerve; and (d) removing said applicator from said patient.

2. The method of claim 1, wherein said exposing step (c) is conducted for less than five minutes.

3. The method of claim 1, wherein said radioactive substance is $Sr_{90}$.

4. The method of claim 3, further comprising shielding said $Sr_{90}$ from said macular tissue prior to said exposing step (c).

5. The method of claim 3 further comprising locating said macular tissue through a fiber optic cable prior to said exposing step (c).

6. The method of claim 1, wherein said distal end portion comprises a curved stem for facilitating insertion between said eye lid and said sclera.

7. A method of radiation therapy for treating macular degeneration of a patient's eye, said eye including a lens, optic nerve and sclera and being located in an eye socket of said patient, comprising:

(a) disposing a therapeutic quantity of a β radiation source having a range less than about 1 cm onto a curved applicator sized to fit between said patient's eye socket and sclera; and (b) exposing a portion of said macular tissue to a dosage of radiation emitted from said β radiation source to irradiate a portion of said macular tissue while not substantially irradiating said patient's lens or optic disc, whereby said macular degeneration is controlled.

8. The method of claim 7, wherein said exposing step is conducted for no more than about two minutes and substantially no radiation is emitted beyond 5 mm from said β radiation source.

9. The method of claim 7, wherein said β radiation source is $Sr_{90}$.

10. The method of claim 9, further comprising shielding said $Sr_{90}$ with less than 1 mm lead- or silver-containing shielding.

11. A radiation therapy applicator, comprising:

(a) proximal and distal end portions, said proximal end portion comprising a handle and said distal end portion comprising a stem having a cavity located at its distal tip, said cavity containing a therapeutically active quantity of a radioactive substance providing a dosage rate of at least about 50 cGr/sec. and a radiation depth of no more than about 5 millimeters.

12. The applicator of claim 10, wherein said radiation source comprises a dose of at least about 80–100 cGr/sec.

13. The applicator of claim 10, wherein said radiation source comprises $Sr_{90}$.

14. The applicator of claim 10, wherein said stem comprises a removable shield for selectively exposing said radiation source.

15. The applicator of claim 10, further comprising a fiber optic cable disposed through said handle and stem portions for locating a macular tissue of a patient's eye.

16. The applicator of claim 14, wherein said radiation source has a half life of at least about 28 years.

17. The applicator of claim 14, further comprising a light source for illuminating a macular tissue through said fiber optic cable.

18. The applicator of claim 17, wherein said fiber optic cable is disposed through said radioactive substance.

19. A radiation therapy applicator, comprising:

proximal and distal end portions, said distal end portion comprising a stem portion having a cavity therein, said cavity containing $Sr_{90}$; said distal end further comprising a selectively removable shield for exposing said $Sr_{90}$ for delivering a dose of radiation to a diseased tissue portion of a patient's eye.

20. The applicator of claim 18, wherein said shield comprises lead or silver.

* * * * *